USOO9953429B2

(12) United States Patent
Mollus et al.

(10) Patent No.: US 9,953,429 B2
(45) Date of Patent: Apr. 24, 2018

(54) MODEL-BASED SEGMENTATION OF AN ANATOMICAL STRUCTURE

(71) Applicant: KONINKLIJKE PHILIPS N.V., Eindhoven (NL)

(72) Inventors: Sabine Mollus, Aachen (DE); Axel Saalbach, Hamburg (DE); Juergen Weese, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/101,018

(22) PCT Filed: Dec. 15, 2014

(86) PCT No.: PCT/EP2014/077660
§ 371 (c)(1),
(2) Date: Jun. 2, 2016

(87) PCT Pub. No.: WO2015/091299
PCT Pub. Date: Jun. 25, 2015

(65) Prior Publication Data
US 2016/0307331 A1    Oct. 20, 2016

(30) Foreign Application Priority Data

Dec. 17, 2013    (EP) ..................................... 13197703

(51) Int. Cl.
*G06K 9/00*    (2006.01)
*G06T 7/00*    (2017.01)
(Continued)

(52) U.S. Cl.
CPC ............ *G06T 7/0089* (2013.01); *G06T 7/149* (2017.01); *G06T 7/344* (2017.01); *G06F 19/321* (2013.01);
(Continued)

(58) Field of Classification Search
CPC ....... G06T 17/00; G06T 19/006; G06T 7/344; G06T 2207/10072; G06T 2207/10121;
(Continued)

(56) References Cited

U.S. PATENT DOCUMENTS 9,697,598 B2 * 7/2017 Serlie .................... G06T 7/0012
2002/0087503 A1 * 7/2002 Judd ................. G06F 17/30244
(Continued)

OTHER PUBLICATIONS

Ecabert, O., et al., "Automatic Model-based Segmentation of the Heart in CT Images". IEEE Transactions on Medical Imaging 2008, 27 (9), pp. 1189-1201.
(Continued)

*Primary Examiner* — Mekonen Bekele

(57) ABSTRACT

A system and method is provided which obtains different medical images (210) showing an anatomical structure of a patient and having been acquired by different medical imaging modalities and/or different medical imaging protocols. The system is configured for fitting a first deformable model to the anatomical structure in the first medical image (220A), fitting a second deformable model to the anatomical structure in the second medical image (220B), mutually aligning the first fitted model and the second fitted model (230), and subsequently fusing the first fitted model and the second fitted model to obtain a fused model (240) by augmenting the first fitted model with a part of the second fitted model which is missing in the first fitted model; or adjusting or replacing a part of the first fitted model based on a corresponding part of the second fitted model having obtained a better fit. The fused model represents a multimodal/multi-protocol segmentation of the anatomical structure, and provides a user with a more comprehensive understanding of the anatomical structure than known models.

14 Claims, 3 Drawing Sheets

(51) Int. Cl.
*G06T 7/33* (2017.01)
*G06T 7/149* (2017.01)
*G06F 19/00* (2018.01)

(52) U.S. Cl.
CPC ........... *G06T 2207/10081* (2013.01); *G06T 2207/10088* (2013.01); *G06T 2207/20124* (2013.01); *G06T 2207/20132* (2013.01); *G06T 2207/30048* (2013.01); *G06T 2210/41* (2013.01)

(58) Field of Classification Search
CPC . G06T 2207/10136; G06T 2207/30048; G06F 19/3437
USPC .......................................... 382/131; 600/443
See application file for complete search history.

(56) References Cited

U.S. PATENT DOCUMENTS

| | | |
|---|---|---|
| 2004/0034283 A1 | 2/2004 | Quaid |
| 2005/0013471 A1* | 1/2005 | Snoeren ............... G06T 7/35 382/131 |
| 2009/0048515 A1* | 2/2009 | Suri ..................... A61B 8/12 600/443 |
| 2009/0063118 A1 | 3/2009 | Dachille et al. |
| 2010/0296709 A1* | 11/2010 | Ostrovsky-Berman . G06T 7/162 382/128 |
| 2011/0170781 A1 | 7/2011 | Bronstein et al. |
| 2011/0178389 A1 | 7/2011 | Kumar et al. |
| 2012/0008763 A1 | 1/2012 | Waalkes et al. |
| 2012/0082354 A1 | 4/2012 | Peters et al. |
| 2012/0087563 A1* | 4/2012 | Ionasec ................ G06T 17/00 382/131 |
| 2012/0230568 A1 | 9/2012 | Grbic et al. |
| 2013/0129174 A1 | 5/2013 | Grbic et al. |
| 2013/0243294 A1* | 9/2013 | Ralovich ............. G06T 7/0012 382/131 |
| 2013/0294667 A1* | 11/2013 | Zheng ................. G06T 7/0012 382/131 |
| 2015/0078645 A1* | 3/2015 | El-Zehiry ............. G06T 7/13 382/131 |
| 2015/0302580 A1* | 10/2015 | Serlie .................. G06T 11/60 382/131 |
| 2016/0267626 A1* | 9/2016 | Allaire .................. G06K 9/52 |
| 2016/0379372 A1* | 12/2016 | Groth .................... G06T 7/12 382/131 |
| 2017/0213338 A1* | 7/2017 | Groth .................. G06T 7/0012 |

OTHER PUBLICATIONS

Chen, Ting et al., "Object-constrained meshless deformable algorithm for high speed 3D nonrigid registration betwee CT and CBCT", Medical Physics, AIP, NY, vol. 37, No. 1, 2009, Abstract.

* cited by examiner

MODEL-BASED SEGMENTATION OF AN ANATOMICAL STRUCTURE

CROSS-REFERENCE TO PRIOR APPLICATIONS

This application is the U.S. National Phase application under 35 U.S.C. § 371 of International Application No. PCT/EP2014/077660, filed on Dec. 15, 2014, which claims the benefit of European Patent Application No. 13197703.5, filed on Dec. 17, 2013. These applications are hereby incorporated by reference herein.

FIELD OF THE INVENTION

The invention relates to a system and method for fitting a deformable model to an anatomical structure in a medical image to obtain a segmentation of the anatomical structure. The invention further relates to a workstation and imaging apparatus comprising the system, and to a computer program product comprising instructions for causing a processor system to perform the method.

BACKGROUND OF THE INVENTION

Robust automatic segmentation of various anatomical structures in a medical image is a key enabler in improving clinical workflows. Here, the term segmentation refers to the identification of the anatomical structure in the medical image by, e.g., delineation of the boundaries of the anatomical structure, or by labeling of the voxels enclosed by the boundaries. Once such segmentation has been performed, it is possible to extract clinical parameters such as, in case of a cardiac structure, ventricular mass, ejection fraction and wall thickness. Consequently, automatic segmentation can significantly reduce the scan-to-diagnosis time, and thus help clinicians in establishing more efficient patient management.

It is known to segment an anatomical structure in a medical image using a deformable model. Such type of segmentation is also referred to as model-based segmentation. The deformable model may be defined by model data. In particular, the model data may define a geometry of the anatomical structure, e.g., in the form of a multi-compartmental mesh of triangles. Inter-patient and inter-phase shape variability may be efficiently accounted for by assigning an affine transformation to each part of such a deformable model. Affine transformations cover translation, rotation, scaling along different coordinate axes and shearing. Moreover, mesh regularity may be maintained by interpolation of the affine transformations at the transitions between different parts of the deformable model. It is noted that such deformable models are also referred to as mean shape models.

The fitting or applying of a deformable model to the image data of the medical image, also referred to as mesh adaptation, may involve optimizing an energy function which may be based on an external energy term which helps to adapt the deformable model to the image data and an internal energy term which maintains a rigidness of the deformable model. It is noted that such an external energy term might make use of boundary detection functions that were trained during a so-termed simulated search, and may model different image characteristics inherent to different medical imaging modalities and/or protocols.

Deformable models of the above described type are known per se, as are methods of applying such models to an anatomical structure in a medical image.

For example, a publication titled *"Automatic Model-based Segmentation of the Heart in CT Images"* by O. Ecabert et al., IEEE Transactions on Medical Imaging 2008, 27(9), pp. 1189-1201, describes a model-based approach for the automatic segmentation of the heart (four chambers, myocardium, and great vessels) from three-dimensional (3D) Computed Tomography (CT) images. Here, model adaptation is performed progressively increasing the degrees-of-freedom of the allowed deformations to improve convergence as well as segmentation accuracy. The heart is first localized in the image using a 3D implementation of the generalized Hough transform. Pose misalignment is corrected by matching the model to the image making use of a global similarity transformation. The complex initialization of the multi-compartment mesh is then addressed by assigning an affine transformation to each anatomical region of the model. Finally, a deformable adaptation is performed to accurately match the boundaries of the patient's anatomy.

SUMMARY OF THE INVENTION

A problem of anatomical modeling is that a segmentation of the anatomical structure, as obtained by the fitting of a deformable model, provides a user with an insufficiently comprehensive understanding of the anatomical structure.

It would be advantageous to obtain a segmentation of the anatomical structure which provides a user with a more comprehensive understanding of the anatomical structure.

To better address this concern, a first aspect of the invention provides a system for fitting a deformable model to an anatomical structure in a medical image to obtain a segmentation of the anatomical structure, comprising:

an image interface for obtaining a first medical image of a patient and a second medical image of the patient, both medical images showing the anatomical structure and having been acquired by different medical imaging modalities or different medical imaging protocols, thereby establishing a different visual representation of the anatomical structure in both medical images;

a processing subsystem configured for:
i) fitting a first deformable model to the anatomical structure in the first medical image, thereby obtaining a first fitted model;
ii) fitting a second deformable model to the anatomical structure in the second medical image, thereby obtaining a second fitted model; wherein the second deformable model differs from the first deformable model for accommodating said different visual representation of the anatomical structure in both medical images;
iii) mutually aligning the first fitted model and the second fitted model, and
iv) after said mutual alignment, fusing the first fitted model and the second fitted model to obtain a fused model.

A further aspect of the invention provides a workstation or imaging apparatus comprising the system.

A further aspect of the invention provides a method for fitting a deformable model to an anatomical structure in a medical image to obtain a segmentation of the anatomical structure, comprising:

obtaining a first medical image of a patient and a second medical image of the patient, both medical images showing the anatomical structure and having been acquired by different medical imaging modalities or different medical imaging protocols, thereby establishing a different visual representation of the anatomical structure in both medical images;

fitting a first deformable model to the anatomical structure in the first medical image, thereby obtaining a first fitted model;

fitting a second deformable model to the anatomical structure in the second medical image, thereby obtaining a second fitted model; wherein the second deformable model differs from the first deformable model for accommodating said different visual representation of the anatomical structure in both medical images;

mutually aligning the first fitted model and the second fitted model, and after said mutual alignment, fusing the first fitted model and the second fitted model to obtain a fused model.

The above measures involve obtaining at least two medical images of a patient which each show an anatomical structure such as an organ, part of an organ, etc. The anatomical structure is represented by the image data of each medical image. The at least two medical images, henceforth also referred to as 'both' medical images, are obtained from different medical imaging modalities and/or different medical imaging protocols. Here, the term 'medical imaging modality' refers to an type of imaging, which includes, but is not limited to, standard (rotational) X-ray Imaging, Computed Tomography (CT), Magnetic Resonance (MR), Ultrasound (US), Positron Emission Tomography (PET), Single Photon Emission Computed Tomography (SPECT), and Nuclear Medicine (NM). Another term for medical imaging modality is medical acquisition modality. Medical imaging employing different medical imaging protocols is also referred to as multi-protocol or multi-parametric imaging. An example of such multi-protocol imaging is the use of different contrast agents and/or tracers to highlight specific anatomical structures in the acquired medical images.

Accordingly, the first medical image may be a CT image and the second medical image may be an MR image. Another example is that the first medical image may be a static CT image and the second medical image may be a multi-phase CT image. Due to the use of different imaging modalities and/or imaging protocols, the anatomical structure is differently represented in both medical images. For example, anatomical information may be well visible in one medical image but less or not visible in the other medical image.

Different deformable models are provided for fitting the anatomical structure in the respective medical images. The deformable models differ in that they take into account that the anatomical structure has a different visual representation in each respective medical image. Such differences may concern, e.g., different mesh topologies, differently defined energy terms, etc. As such, each deformable model may take into account the visual properties of the anatomical structure when acquired by the respective imaging modality and/or imaging protocol. For example, the first deformable model may have been generated for fitting the visual representation of a heart in a CT image whereas the second deformable model may have been generated for fitting the heart in a MR image.

The deformable models are applied to the anatomical structure in the respective medical images. As a result, a first fitted model is obtained segmenting the anatomical structure in the first medical image and a second fitted model is obtained segmenting the anatomical structure in the second medical image. It is noted that due to the difference in deformable model and the difference in visual representation of the anatomical structure in both medical images, both fitted models typically differ in shape.

The fitted models are mutually aligned. As a result of the mutual alignment, a commonly positioned part of both fitted models corresponds to a same part of the anatomical structure. It is noted that such alignment may be based on a matching of commonalities between the fitted models, i.e., using a model-based registration. Alternatively or additionally, the alignment may be based on a matching of commonalities between the first medical image and the second medical image, i.e., using an image-based registration.

After being mutually aligned, the fitted models are fused. As a result, a fused model is obtained which represents a result of the fusion of the fitted models. Here, the term 'fusion' refers to information from the fitted models, in particular shape information, being combined so as to obtain the fused model. A non-limiting example may be that different parts of the fused model may originate from either the first fitted model or the second fitted model.

The inventors have recognized that, nowadays, many clinical decisions are not based on a single modality or protocol anymore. Instead, the image data of different imaging modalities and/or imaging protocols is studied to receive a more comprehensive understanding of an anatomical structure, such as its morphology and function. By fusing the deformable models after being fitted to medical images obtained from different imaging modalities and/or imaging protocols, a clinician who would like to obtain a comprehensive understanding of an anatomical structure does not need to refer anymore to the segmentation results of different medical workstations. Rather, the fused model represents a multi-modal and/or multi-protocol segmentation of the anatomical structure. Advantageously, it is not needed to mentally fuse separately obtained modeling results into a single model. Advantageously, it is not needed to perform measurements, interact with the model, etc., for each modality separately. Rather, such actions may be applied to the (single) fused model.

U.S. 2012/0230568 A1 describes a model-based fusion of multi-modal volumetric images. However, this differs from the present invention as U.S. 2012/0230568 A1 uses differences between models estimated from multi-modal images to obtain a transformation for enabling the different images to be fused into a single image.

Optionally, the processing subsystem is configured for fusing the first fitted model and the second fitted model by:
i) augmenting the first fitted model with a part of the second fitted model which is missing in the first fitted model; or
ii) adjusting or replacing a part of the first fitted model based on a corresponding part of the second fitted model having obtained a better fit.

By augmenting or replacing part of the first fitted model with a part of the second fitted model, a hybrid fused model is obtained, i.e., incorporating parts of different fitted models. By adjusting part of the first fitted model based on a corresponding part of the second fitted model, model information of a different fitted model is used to modify the first fitted model, thereby obtaining the fused model. These options are well suited for obtaining a fused model which represents a multi-modal segmentation of the anatomical structure. It is noted that in order to evaluate such a better fit, the processing subsystem may make use of a goodness-of-fit function or similar type of quality evaluation function.

Optionally, the system further comprises a visualization subsystem for visualizing the fused model. The visualization subsystem allows the fused model to be visualized to a user such as a clinician. For example, the visualization subsystem may generate display data which, when displayed on a display, displays the fused model. It is noted that the display may, but does not need to, be part of the visualization subsystem.

Optionally, the visualization subsystem is configured for visualizing the fused model by overlaying the fused model over a displayed image, the displayed image being at least one of the group of: the first medical image, the second medical image, and a fused medical image obtained by an image fusion of the first medical image and the second medical image. By overlaying the fused model over the displayed image, the user is enabled to obtain a more comprehensive understanding of the anatomical structure. In this respect, it is noted that the image fusion of the first medical image and the second medical image may be performed based on segmentation provided by the fused model.

Optionally, the visualization subsystem is configured for processing the displayed image based on the fused model. Since the fused model represents a multi-modal and/or multi-protocol segmentation of the anatomical structure which is deemed to better model the anatomical structure than either of the fitted models individually, said fused model may be advantageously used in further processing the displayed image. For example, an image enhancement may be applied based on the segmentation provided by the fused model. Another example is that the fused model may be used to better segment the anatomical structure in the displayed image.

Optionally, the visualization subsystem is configured for processing the displayed image by cropping the displayed image based on anatomical information derived from the fused model. By cropping the displayed image based on such anatomical information, unnecessary image data can be omitted from display. Advantageously, the cognitive burden of interpreting the displayed image is reduced.

Optionally, the processing subsystem is configured for determining a discrepancy between the first fitted model and the second fitted model, wherein the visualization subsystem is configured for visualizing the discrepancy in visual relation with the fused model. Such a discrepancy may be of clinical relevance and is therefore visualized. By visualizing the discrepancy in visual relation with the fused model, the cognitive burden of interpreting the discrepancy is reduced.

Optionally, the visualization subsystem is configured for visualizing the discrepancy by visually coding a display of the fused model. Here, the term 'visually coding' refers to adapting the display of the fused model to visualize the discrepancy. For example, a color coding of the fused model may be used to visually indicate the location or the magnitude of the discrepancy.

Optionally, the first medical image is constituted by a time-series of images, wherein the first deformable model is arranged for modeling a change in the anatomical structure over the time-series of images, and wherein the visualization subsystem is configured for visually representing the change in the visualizing of the fused model. For example, the first medical image may be a four-dimensional (4D) image consisting of a series of three-dimensional (3D) images acquired at different times, e.g., at different cardiac phases. By determining the change in the anatomical structure across the series and visualizing said change in the fused model, the user can conveniently, i.e., with little cognitive burden, obtain a comprehensive overview of the anatomical structure together with the change in the anatomical structure.

Optionally, the visualization subsystem is configured for animating the fused model to visually represent the change. Such animating of the fused model is well suited for visualizing the change in the anatomical structure.

Optionally, the system further comprises a user interaction subsystem for enabling a user to interact with the fused model. For example, the user may use a pointer to select, drag or otherwise interact with (a part of) the fused model.

Optionally, the user interaction subsystem is configured for carrying out an action with respect to a part of, one of the group of: the first medical image, the second medical image, the first fitted model and the second fitted model, based on the user interacting with a corresponding part of the fused model. Hence, an action is carried out with respect to a part of either medical image, i.e., with respect to a location therein, or a part of either fitted model, based on the user interacting with a corresponding part of the fused model. For example, the user may add an annotation to a selected part of the fused model which causes the annotation to be added to a location the first medical image which corresponds, i.e., represents similar content, to the part of the fused model.

In summary, a system is provided which obtains different medical images showing an anatomical structure of a patient and having been acquired by different medical imaging modalities and/or different medical imaging protocols. The system is configured for fitting a first deformable model to the anatomical structure in the first medical image, fitting a second deformable model to the anatomical structure in the second medical image, mutually aligning the first fitted model and the second fitted model, and subsequently fusing the first fitted model and the second fitted model to obtain a fused model. The fused model represents a multi-modal/multi-protocol segmentation of the anatomical structure, and provides a user with a more comprehensive understanding of the anatomical structure than known models. It will be appreciated by those skilled in the art that two or more of the above-mentioned embodiments, implementations, and/or aspects of the invention may be combined in any way deemed useful.

Modifications and variations of the system and/or the computer program product, which correspond to the described modifications and variations of the method, can be carried out by a person skilled in the art on the basis of the present description.

A person skilled in the art will appreciate that the invention may be applied to multi-dimensional image data, e.g. to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
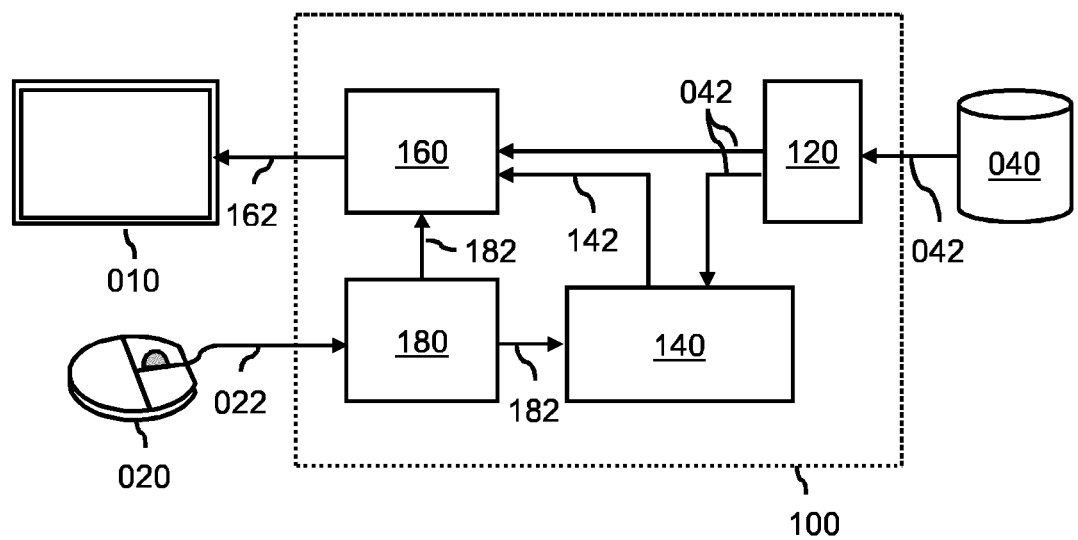
FIG. 1 shows a system for obtaining a fused model by fitting different deformable models to different medical images and subsequently fusing the fitted models, with the system further comprising a visualization subsystem for visualizing the fused model and a user interaction subsystem for enabling a user to interact with the fused model.

FIG. 1 shows a system 100 for fitting a deformable model to an anatomical structure in a medical image to obtain a segmentation of the anatomical structure. The system 100 comprises an image interface 120 for obtaining a first medical image of a patient and a second medical image of the patient. Both medical images show the anatomical structure and having been acquired by different medical imaging modalities or medical imaging protocols, thereby establishing a different visual representation of the anatomical structure in both medical images. FIG. 1 shows the image interface 120 obtaining the medical images in the form of image data 042 from an external database 040, such as a Picture Archiving and Communication System (PACS). As such, the image interface 120 may be constituted by a so-termed DICOM interface. However, the image interface 120 may also take any other suitable form, such as a memory or storage interface, a network interface, etc.

The system 100 further comprises a processing subsystem 140. The processing subsystem 140 is configured for, during operation of the system 100, fitting a first deformable model to the anatomical structure in the first medical image, thereby obtaining a first fitted model, and fitting a second deformable model to the anatomical structure in the second medical image, thereby obtaining a second fitted model. Such deformable models may be available to the processing subsystem 140 in the form of model data, defining, e.g., a mesh topology, one or more energy terms for fitting the mesh to the image data, etc. The processing subsystem 140 is further arranged for mutually aligning the first fitted model and the second fitted model, and after said mutual alignment, fusing the first fitted model and the second fitted model to obtain a fused model. The processing subsystem 140 may then make the fused model available, e.g., by outputting model data 142 defining the fused model.

In accordance with an optional aspect of the present invention, FIG. 1 shows the system 100 further comprising a visualization subsystem 160 for visualizing the fused model. For that purpose, the visualization subsystem 160 is shown to receive the model data 142 from the processing subsystem 140, and to provide display data 162 to a display 010. The visualization subsystem 160 may visualize the fused model by overlaying the fused model over a displayed image. The displayed image may constituted by, e.g., the first medical image, the second medical image, or a fused medical image obtained by an image fusion of the first medical image and the second medical image. For that purpose, the visualization subsystem 160 may receive image data 042 from the image interface 120.

In accordance with a further optional aspect of the present invention, FIG. 1 shows the system 100 further comprising a user interaction subsystem 180 for enabling a user to interact with the fused model. For example, a user may operate a user input device 020 such as a computer mouse, keyboard, touch screen, etc., thereby providing user input 022 to the system 100 representing user commands 182. Upon receiving such user commands 182, the processing subsystem 140 may carry out an action with respect to a part of the first medical image, the second medical image and/or the first fitted model and the second fitted model, based on the user interacting with a corresponding part of the fused model.

It is noted that the operation of the system 100, including various optional aspects thereof, will be further described with reference to FIGS. 4 and 5A, 5B and 5C.

Figure 2:
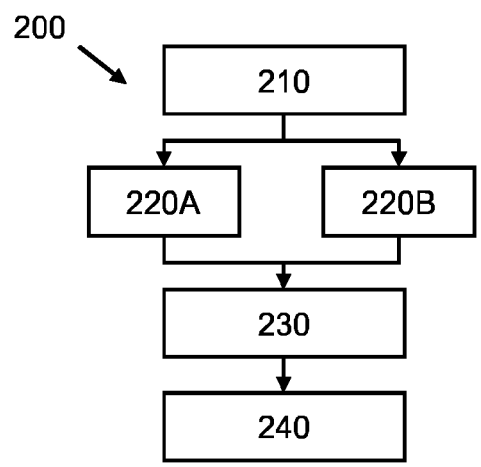
FIG. 2 shows a method for obtaining the fused model.

FIG. 2 shows a method 200 for fitting a deformable model to an anatomical structure in a medical image to obtain a segmentation of the anatomical structure. The method 200 comprises, in a step titled "OBTAINING MEDICAL IMAGES", obtaining 210 a first medical image of a patient and a second medical image of the patient, both medical images showing the anatomical structure and having been acquired by different medical imaging modalities or medical imaging protocols, thereby establishing a different visual representation of the anatomical structure in both medical images. The method 200 further comprises, in a step titled "FITTING FIRST DEFORMABLE MODEL TO FIRST MEDICAL IMAGE" fitting 220A a first deformable model to the anatomical structure in the first medical image, thereby obtaining a first fitted model. The method 200 further comprises, in a step titled "FITTING SECOND DEFORMABLE MODEL TO SECOND MEDICAL IMAGE", fitting 220B a second deformable model to the anatomical structure in the second medical image, thereby obtaining a second fitted model; wherein the second deformable model differs from the first deformable model for accommodating said different visual representation of the anatomical structure in both medical images. The method 200 further comprises, in a step titled "MUTUALLY ALIGNING THE FITTED MODELS", mutually 230 aligning the first fitted model and the second fitted model. The method 200 further comprises, in a step titled "FUSING THE FITTED MODELS", after said mutual alignment, fusing 240 the first fitted model and the second fitted model to obtain a fused model.

It is noted that the above steps may be performed in any suitable order. For example, the steps of fitting 220A the first deformable model and fitting 220B the second deformable model may be performed simultaneously or sequentially. Moreover, the step of mutually 230 aligning the first fitted model and the second fitted model may be performed by aligning the medical images themselves, which may be performed before, during, or after fitting 220A the first deformable model and fitting 220B the second deformable model.

Figure 3:
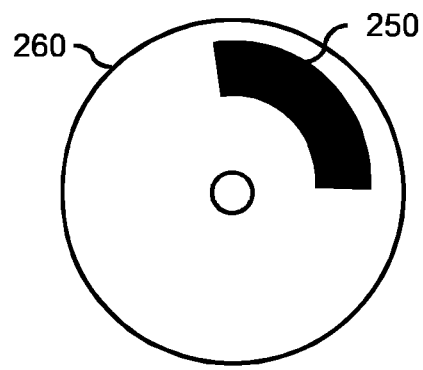
FIG. 3 shows a computer program product comprising instructions for causing a processor system to perform the method.

FIG. 3 shows a computer program product comprising instructions for causing a processor system to perform the method of FIG. 2, i.e., comprising a computer program. The computer program may be comprised in a non-transitory manner on a computer readable medium 260, e.g., as a series 250 of machine readable physical marks and/or as a series of elements having different electrical, e.g., magnetic, or optical properties or values.

The operation of the system of FIG. 1 and the method of FIG. 2, including various optional aspects thereof, may be explained in more detail as follows.

Figure 4:
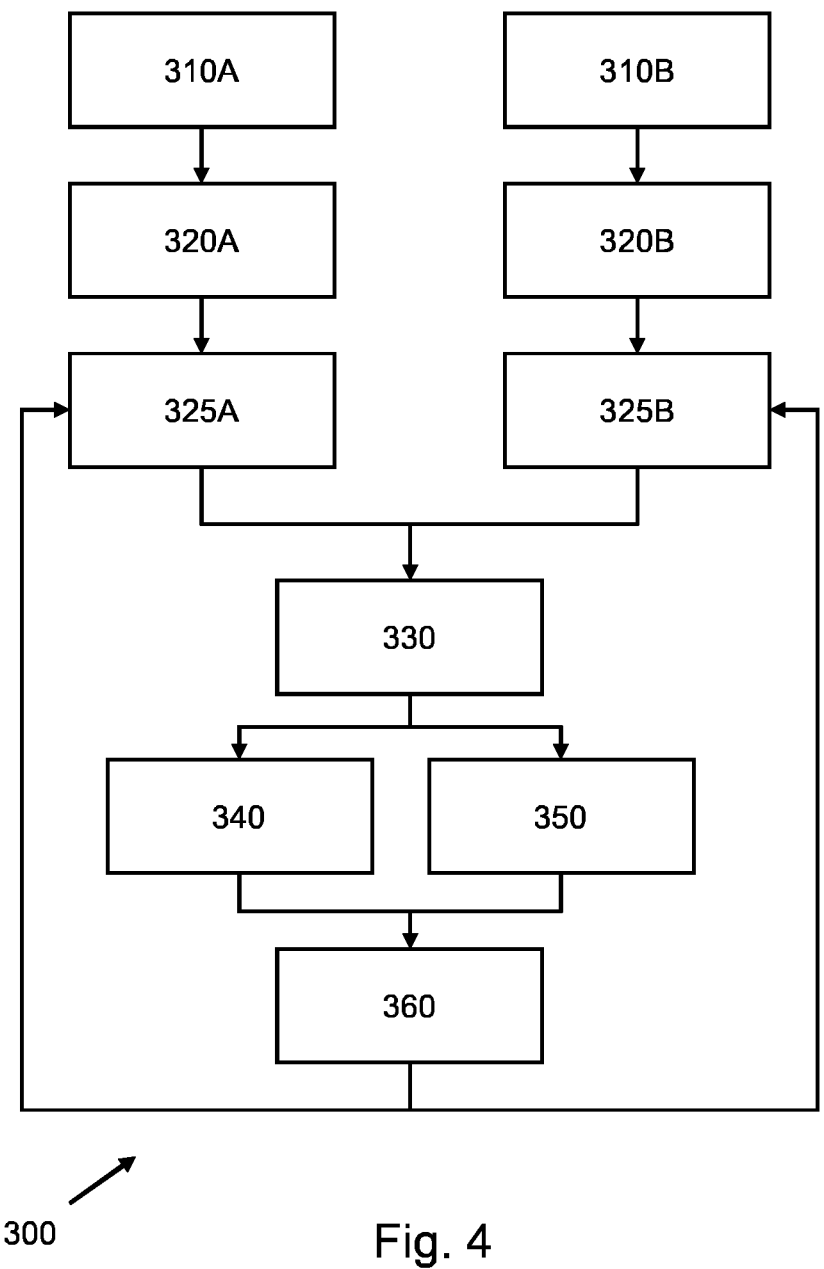
FIG. 4 shows a flow diagram of an embodiment of the present invention.

FIG. 4 shows a flow diagram of an embodiment of the present invention. The embodiment illustrates two cardiac clinical application scenarios in which the invention may be advantageously applied, namely the viewing and analysis of an 2D/3D/4D echocardiography dataset in relation to a 3D Multi-Slice CT (MSCT) dataset. Here, the term 'dataset' refers to image data representing at least one medical image. Consequently, fitting a deformable model to a dataset refers to the deformable model being fitted to at least one medical image of the dataset. It is noted that in cases where the dataset represents a time-series or other series of medical images, e.g., showing the heart across different cardiac phases, fitting a deformable model to the dataset may comprise fitting a deformable model to each medical image, thereby obtaining a segmentation of the heart in each of the different cardiac phases. This may be the case if, e.g., the echocardiography dataset is a 4D dataset.

Initially, in a step 310A, a reference dataset is acquired, e.g., from a cardiac MSCT angiography. In a further step 320A, the reference dataset may be segmented using a dedicated CT model, i.e., by fitting the CT model to the reference dataset. As a result, a personalized CT-specific model may be obtained, i.e., a first fitted model represented by a mesh. In a step 310B, a further dataset of the same patient may be acquired, e.g., from a Transesophageal Echocardiogram (TEE) study consisting of 2D, 3D and 4D image data or a rotational C-arm CT with a selective contrast agent injection. In a further step 320B, the further dataset may be segmented using one or more dedicated model(s), resulting in at least one more fitted models, i.e., at least a second fitted model. The first fitted model and the second fitted model may then both be fused in a step 340 to obtain a fused model.

However, to first mutually align the different fitted models, a number of processing steps may be performed, commonly denoted as step 325A for the first fitted model and step 325B for the second fitted model. These steps may comprise:
1. Roughly aligning the first fitted model and the second fitted model. This constitutes a registration problem, and more specifically a mesh-to-mesh or segmentation-based registration problem. To solve such a problem, Iterative Closest Point (ICP)-based algorithms may be used. Such algorithms may be adapted to take into account differences, e.g., in mesh topology, between both fitted models. For example, the first fitted model may comprise a dynamic heart valve structure which is not part of the second fitted model. For that purpose, an anatomy-specific (binary) weighting scheme may be employed.
2. Refining the registration based on matching of pre-defined anchor structures, such as, e.g., the aortic root or the mitral valve annulus, to each other. In the earlier mentioned case of CT/TEE mitral valve fusion, such refinement may be as follows. Since CT is geometrically more accurate and is able to image a full heart, the deformable model fitting this dataset may be used as a geometrical reference. A TEE/Doppler of the mitral valve shows only parts of the Left Atria (LA) and the Left Ventricle (LV) but the complete mitral valve in high temporal resolution. A segmentation of this dataset may result in a set of meshes that represent the motion of the valve leaflets together with a crude segmentation of the surrounding structure. Both datasets jointly show the mitral valve annulus which may therefore be used as anchor structures. A (elastic) deformation may be applied to the TEE meshes to conform to the geometry of the reference CT/MR mesh. The same (inherited) deformation may be applied to the leaflet mesh structures in the TEE meshes so that the anchor structures match and the complementary valve leaflet structures fit the geometry of the reference mesh. This deformation may be described as optimization problem that minimizes an energy term that is composed of an internal and an external energy part.

After having mutually aligned the first fitted model and the second fitted model, the first fitted model and the second fitted model may then both be fused in a step 340 to obtain a fused model. Such fusion may involve augmenting the first fitted model with a part of the second fitted model which is missing in the first fitted model, and/or adjusting or replacing a part of the first fitted model based on a corresponding part of the second fitted model having obtained a better fit. For that purpose, a meshing toolkit may be used to cut and glue meshes with respect to anatomical labels and application-specific settings. It is noted that such meshing toolkits are known per se from the field of medical image segmentation. In the context of this embodiment, a result may be a fused TEE/CT model which comprises the high-resolution full heart geometry from the reference CT and the valve dynamics from TEE.

Finally, in a step 360, the fused model may be visualized. Such visualization may also involve visualizing a discrepancy between the first fitted model and the second fitted model in visual relation with the fused model. Such a discrepancy may be determined in step 350. As a result, the fused model may be color-coded, e.g., so as to visually indicate a remaining local Euclidean distance between both fitted models. The fused model may be overlaid over an image, such as a first medical image from the first dataset or a second medical image from the second dataset. Both medical images may also be fused, with the fused model being overlaid over the fused medical image. In particular, such image fusion may be performed based on the fused model. Additionally or alternatively, the displayed image may be processed based on the fused model. For example, the displayed image may be cropped based on anatomical information derived from the fused model. Another example is that the anatomical structure in the displayed image may be further segmented using the fused model. For example, in the context of this embodiment, the TEE dataset may be cropped to only show the valve motion or the Doppler velocity measurements along with the reference CT. Various other types of processing are equally conceivable.

Figure 5A:
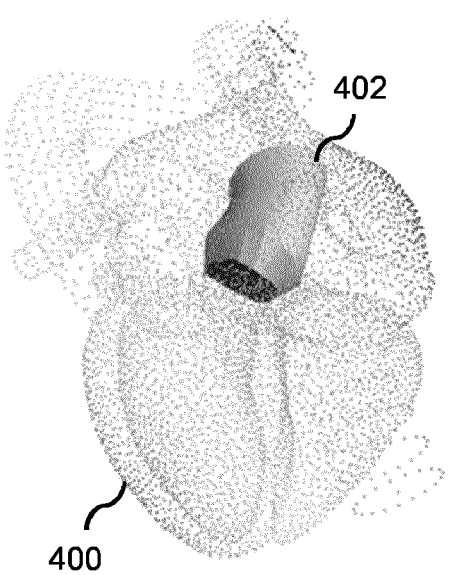
FIG. 5A shows an example of a first fitted model in the form of a high-resolution full heart model with a flat annular plane dedicated to static CT.
Figure 5B:
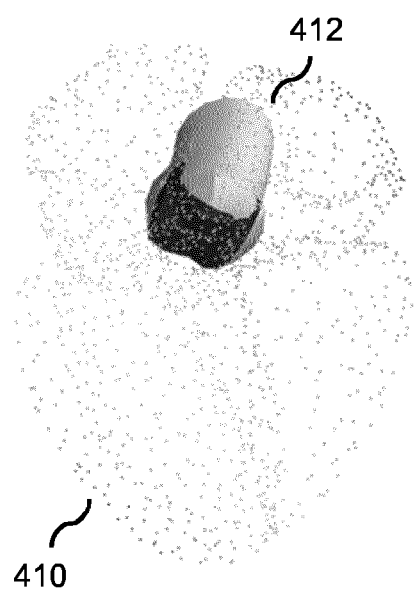
FIG. 5B shows an example of a second fitted model in the form of medium-resolution heart model with dynamic aortic valve model dedicated to 4D TEE.
Figure 5C:
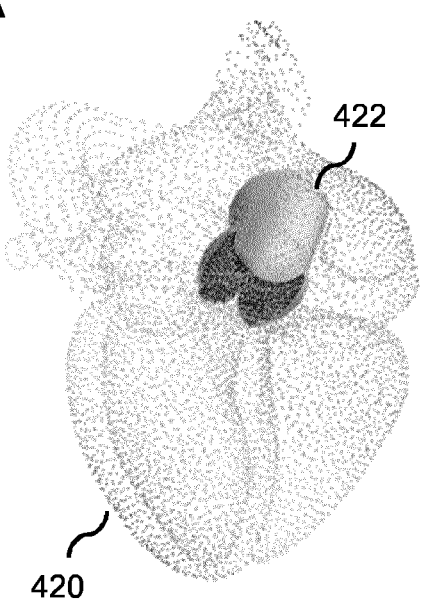
FIG. 5C shows a fused model in the form of a high resolution full heart model with dynamic aortic valve model, obtained by fusing the first fitted model and the second fitted model.

It is further noted such fusion may involve fusing a dynamic model, i.e., a deformable model which is arranged for modeling a change in the anatomical structure, with a static model. Such fusion is shown in FIGS. 5A-5C. Here, FIG. 5A shows an example of a first fitted model 400 in the form of a high-resolution full heart model with a flat annular plane dedicated to static CT. Here, the fitted model 400 is shown as a point-cloud of nodes representing a mesh, with a part 402 of the mesh being rendered using non-translucent surfaces so as to better visualize said part. FIG. 5B shows an example of a second fitted model 410 in the form of a medium-resolution heart model with dynamic aortic valve model 412 dedicated to 4D TEE. FIG. 5C shows a fused model 420 in the form of a full heart model with dynamic aortic valve model 422, obtained by fusing the first fitted model and the second fitted model. In such a case, i.e., when one of the deformable models is arranged for modeling a change in the anatomical structure over a series of images, this change may be visualized in the fused model 420. For example, the fused model 420 may be animated or color-coded to visualize the change.

In general, the user may be enabled to interact with the fused model. For example, when visualizing discrepancies between the fitted models in the fused model, the user may be enabled to apply a local correction to the fused model, which may be used as feedback in the fitting of the deformable models as well as in the fusion of the subsequently fitted models. The processing subsystem may also be configured for carrying out an action with respect to either of the medical images or either of the fitted models based on the user interacting with a corresponding part of the fused model. For example, a landmark set by the user in a medical image showing the fused model may be propagated to another medical image by means of the fused model. Also, an annotation or measurement as generated by the user may be visualized in an aligned way across several medical images.

It will be appreciated that the present invention may be advantageously used in the following other application scenarios:

A volume part showing color-flow Doppler information in TEE may be extracted and overlaid over a static CT mesh;

A segmentation of a TEE volume showing, e.g., only parts of the left ventricle and parts of the left atrium, may be auto-completed by the full heart anatomy represented in the CT mesh; and An interventional rotational C-arm CT segmentation showing selective parts of the patient's heart contrast enhanced and this giving an accurate update of the pose of the patient's heart may be auto-completed and accomplished by the anatomy represented in a respective pre-interventional CT data set.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for fitting a deformable model to an anatomical structure in a medical image to obtain a segmentation of the anatomical structure, comprising:
   an image interface for obtaining a first medical image of a patient and a second medical image of the patient, both medical images showing the anatomical structure and having been acquired by different medical imaging modalities or different medical imaging protocols, thereby establishing a different visual representation of the anatomical structure in both medical images;
   a processing subsystem configured for:
   i) fitting a first deformable model to the anatomical structure in the first medical image, thereby obtaining a first fitted model;
   ii) fitting a second deformable model to the anatomical structure in the second medical image, thereby obtaining a second fitted model; wherein the second deformable model differs from the first deformable model for accommodating said different visual representation of the anatomical structure in both medical images;
   iii) mutually aligning the first fitted model and the second fitted model, and
   iv) after said mutual alignment, fusing the first fitted model and the second fitted model to obtain a fused model,
   wherein the processing subsystem is configured for mutually aligning the first fitted model and the second fitted model by:
   i) roughly aligning the first fitted model and the second fitted model, and
   ii) refining the alignment based on matching of predefined anchor structures depicted in both medical images, the anchor structures being subsets of the medical images, wherein a deformation is calculated to match the anchor structure of the second fitted model to the anchor structure of the first fitted model, and wherein the calculated anchor structure deformation is applied to the second fitted model in its entirety.

2. The system according to claim 1, wherein the processing subsystem is configured for fusing the first fitted model and the second fitted model by, augmenting the first fitted model with a part of the second fitted model which is missing in the first fitted model; or adjusting or replacing a part of the first fitted model based on a corresponding part of the second fitted model having obtained a better fit;

further comprising a visualization subsystem for visualizing the fused model.

3. The system according to claim 2, wherein the visualization subsystem is configured for visualizing the fused model by overlaying the fused model over a displayed image, the displayed image being at least one of the group of: the first medical image, the second medical image, and a fused medical image obtained by an image fusion of the first medical image and the second medical image.

4. The system according to claim 3, wherein the visualization subsystem 160 is configured for processing the displayed image based on the fused model.

5. The system according to claim 4, wherein the visualization subsystem is configured for processing the displayed image by cropping the displayed image based on anatomical information derived from the fused model.

6. The system according to claim 2, wherein the processing subsystem is configured for determining a discrepancy between the first fitted model and the second fitted model, wherein the visualization subsystem is configured for visualizing the discrepancy in visual relation with the fused model.

7. The system according to claim 6, wherein the visualization subsystem is configured for visualizing the discrepancy by visually coding a display of the fused model.

8. The system according to claim 2, wherein the first medical image is constituted by a time-series of images, wherein the first deformable model is arranged for modeling a change in the anatomical structure over the time-series of images, and wherein the visualization subsystem is configured for visually representing the change in the visualizing of the fused model.

9. The system according to claim 8, wherein the visualization subsystem is configured for animating the fused model to visually represent the change.

10. The system according to claim 2, further comprising a user interaction subsystem for enabling a user to interact with the fused model.

11. The system according to claim 10, wherein the processing subsystem is configured for carrying out an action with respect to a part of, one of the group of: the first medical image, the second medical image, the first fitted model and the second fitted model, based on the user interacting with a corresponding part of the fused model.

12. Workstation or imaging apparatus comprising the system according to claim 1.

13. A method for fitting a deformable model to an anatomical structure in a medical image to obtain a segmentation of the anatomical structure, comprising:

obtaining a first medical image of a patient and a second medical image of the patient, both medical images showing the anatomical structure and having been acquired by different medical imaging modalities or different medical imaging protocols, thereby establishing a different visual representation of the anatomical structure in both medical images;

fitting a first deformable model to the anatomical structure in the first medical image, thereby obtaining a first fitted model;

fitting a second deformable model to the anatomical structure in the second medical image, thereby obtaining a second fitted model; wherein the second deformable model differs from the first deformable model for accommodating said different visual representation of the anatomical structure in both medical images;

mutually aligning the first fitted model and the second fitted model by i) roughly aligning the first fitted model and the second fitted model, and ii) refining the alignment based on matching of predefined anchor structures depicted in both medical images, the anchor structures being subsets of the medical images, wherein a deformation is calculated to match the anchor structure of the second fitted model to the anchor structure of the first fitted model, and wherein the calculated anchor structure deformation is applied to the second fitted model in its entirety; and fusing the first fitted model and the second fitted model to obtain a fused model.

14. A computer program product comprised in a non-transitory computer readable medium comprising instructions for causing a processor system to perform the method according to claim 13.

* * * * *